United States Patent [19]

Funakoshi et al.

[11] 4,039,572

[45] Aug. 2, 1977

[54] PROCESS FOR PREPARING DIESTERS OF CARBOXYLIC ACIDS BY CATALYTIC OXIDATIVE CARBONYLATION

[75] Inventors: Wataru Funakoshi; Takanori Urasaki; Hiroshi Fujimoto, all of Iwakuni, Japan

[73] Assignee: Teijin Limited, Osaka, Japan

[21] Appl. No.: 558,555

[22] Filed: Mar. 14, 1975

[30] Foreign Application Priority Data

Mar. 19, 1974 Japan .................................. 49-30559
Mar. 20, 1974 Japan .................................. 49-30890
June 22, 1974 Japan .................................. 49-70791
June 22, 1974 Japan .................................. 49-70792

[51] Int. Cl.$^2$ ............................................. C07C 67/38
[52] U.S. Cl. ............................ 260/468 K; 260/468 L; 260/468 M; 260/473 A; 260/475 FR; 260/475 SC; 260/479 R; 260/479 S; 260/476 R; 260/484 R; 260/485 R; 260/485 L; 260/486 AC
[58] Field of Search ........ 260/485 R, 468 M, 475 SC, 260/533 AN, 468 K, 468 L, 475 FR

[56] References Cited

U.S. PATENT DOCUMENTS

| | | | |
|---|---|---|---|
| 3,176,038 | 3/1965 | Zachry et al. | 260/485 R |
| 3,367,961 | 2/1968 | Brewbaker | 260/485 R |
| 3,397,226 | 8/1968 | Fenton | 260/486 |
| 3,626,005 | 12/1971 | Scheben et al. | 260/468 M |
| 3,887,595 | 6/1975 | Nozaki | 260/485 R |

Primary Examiner—Jane S. Myers
Attorney, Agent, or Firm—Sherman & Shalloway

[57] ABSTRACT

A process for preparing diesters of carboxylic acids by oxidative carbonylation of $C_2$–$C_{20}$ olefins, $C_1$–$C_{20}$ monohydric aliphatic alcohols and carbon monoxide in an atmosphere containing molecular oxygen at a temperature of from room temperature to about 350° C. in the presence of a carrier-supported catalyst containing a platinum group metal, wherein said catalyst comprises, supported on a carrier, a post-reduced compound of a platinum group metal and a post-reduced compound of a metal having an atomic number of not less than 22 selected from the group consisting of metals of Groups Ib, IIb, III, IV, V, VI and VIIb of the periodic table.

9 Claims, No Drawings

PROCESS FOR PREPARING DIESTERS OF CARBOXYLIC ACIDS BY CATALYTIC OXIDATIVE CARBONYLATION

This invention relates to an improved process for preparing diesters of carboxylic acids by catalytic oxidative carbonylation in improved yields and selectivities.

More specifically, this invention relates to a process for preparing diesters of carboxylic acids by oxidative carbonylation of $C_2$–$C_{20}$ olefins, $C_1$–$C_{20}$ monohydric aliphatic alcohols and carbon monoxide at a temperature ranging from room temperature to about 350° C. in an atmosphere containing molecular oxygen in the presence of a carrier-supported catalyst containing a platinum group metal, said catalyst comprising on a carrier a post-reduced compound containing a platinum group and a post-reduced compound of a metal having an atomic number of not less than 22 selected from the group consisting of metals of Groups Ib, IIb, III, IV, V, VI and VIIb of the periodic table.

Direct methods for producing esters of carboxylic acids by oxidative carbonylation of olefins, monohydric aliphatic alcohols and carbon monoxide at room temperature to about 350° C. in an atmosphere containing molecular oxygen in the presence of a catalyst containing a platinum group metal are known (for example, see U.S. Pat. Nos. 3,397,225, 3,397,226, 3,530,188, 3,625,995, and 3,755,421).

In such known methods, the oxidative carbonylation is carried out in the presence of a catalyst containing a platinum group metal such as a platinum metal itself, a soluble salt thereof, a chelate thereof, a complex thereof with a biphyletic ligand such as phosphines, in the presence or absence of quinones or an oxide of a nitrogen containing organic compound such as nitro or nitroso compounds. In order to maintain the platinum group metal in its elevated oxidation state, the conjoint use of a polyvalent heavy metal salt having an oxidation potential more positive than platinum group metals as a redox agent is recommended in these methods. These prior methods teach that the redox agent maintains the platinum group metal contained in the catalyst in its elevated oxidation state, and on the other hand, molecular oxygen oxidizes and regenerates the redox agent. The redox agent is specifically exemplified, for example, in U.S. Pat. No. 3,755,421 as carboxylates, nitrates, sulfates and halides of Cu, Fe, Mn, Co, Hg, Ni, Cr, Mo, V or Ta which belong to metals of Groups Ib, IIb, Vb, VIb, VIIb and VIII.

U.S. Pat. No. 3,397,226 discloses that the reaction is preferably carried out in the liquid phase, but when it is carried out in the vapor phase, a catalyst supported on an inert carrier such as alumina, silica, titania, zirconia, or alumino-silicate can be used.

As to carrier-supported catalysts, the U.S. Pat. No. 3,755,421 discloses that the noble metal can be distended on the carrier by impregnation of the carrier with a solution of salt, complex or chelate of the noble metal, and that the impregnation can be achieved by evaporating the solvent from the admixture of inert carrier and catalyst solution or by addition of a precipitating agent to form an insoluble salt or hydroxide of the noble metal, and that the catalyst is thereafter dried and can be used in the oxidative carbonylation.

None of the examples in the prior art methods disclose the use of carrier-supported catalysts. Furthermore, in these prior proposals, palladium chloride or palladous chloride as a soluble salt of noble metal and a redox agent such as cupric chloride are used in the presence or absence of the cocatalyst or biphyletic ligand. As to catalysts supported on an inert carrier, the prior art merely discloses that a noble metal compound is supported on a carrier, and then dried, and used directly in carbonylation reactions. No disclosure or suggestion is found in the prior art about the use of carrier-supported catalysts which have been reduced. In particular, the prior art does not disclose at all catalysts obtained by supporting a platinum group metal-containing compound and a polyvalent heavy metal salt on a carrier, and reducing the product, that is, the post-reduced compound of platinum group metal and the post-reduced heavy metal salt supported on a carrier. Naturally, therefore, no information is given in the prior art which suggests that the use of such a post-reduced catalyst supported on a carrier would bring about some improvement.

The use of a soluble salt of platinum group metal without being supported on a carrier is disadvantageous, because very complicated procedures are involved in separating the product from the reaction mixture and for separating and recovering the catalyst from the mixture regenerating the salt. Furthermore, according to this method, it is extremely difficult to recover and regenerate expensive noble metals without any loss, and this adds to an increased cost of the final product. In addition, these methods require the use of a reactor made of titanium which is expensive, in order to prevent the corrosion of the reactor by large quantities of halide ions contained in the reaction system. Moreover, the yields and selectivities of the products obtained in the prior art methods are not satisfactory, and require further improvements.

Our investigation regarding the above oxidative carbonylation in the presence of a catalyst containing a platinum group metal led to the discovery that the use of a catalyst comprising, supported on a carrier, a post-reduced compound of a platinum group metal and a post-reduced compound of a metal having an atomic number of not less than 22 selected from the group consisting of metals of Groups Ib, IIb, III, IV, V, VI and VIIb can overcome the various disadvantages caused by the unsupported catalysts, but also makes it possible to perform the above catalytic carbonylation reaction with improved yields and selectivities.

According to the technical expedient of the prior art in which a redox agent is used in order to maintain the platinum group metal in its elevated oxidation state, the use of a platinum group metal compound and a specific metal compound, which are post-reduced, on a carrier might be expected to bring about worse results, and would not be expected to give an improvement. As a matter of fact, the prior art only discloses that a catalyst compound supported on a carrier without being reduced is dried, and directly used in the reactions, and gives no examples about the use of carrier-supported catalysts. In view of such prior art proposals and technical concept, the increased yields and selectivities achieved by the method of this invention are quite unexpected and surprising.

Accordingly, it is an object of this invention to provide a process for preparing diesters of carboxylic acids from olefins, monovalent aliphatic alcohols and carbon monoxide by catalytic oxidative carbonylation in improved yields and selectivity and with operating and equipment advantages.

Other objects and advantages of this invention will become more apparent from the following description.

The reaction in this invention, for example, can be shown schematically as follows:

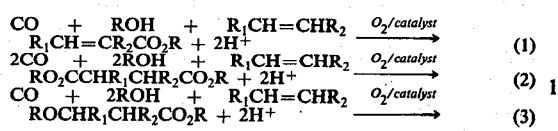

In the above reaction equations, R represents an alkyl, cycloalkyl, aryl, aralkyl or alkaryl group, and $R_1$ and $R_2$ represent a hydrogen atom or an alkyl or aryl group.

The acid portion of the ester obtained is derived from the olefin as shown in the above reaction equations.

When the ester to be obtained is an unsaturated carboxylic acid ester, the acid portion has 1 more carbon atom than the starting olefin. When the ester is a dicarboxylic acid ester in accordance with reaction equation (2), the acid portion has 2 more carbon atoms than the starting olefin. When the ester is a β-alkoxycarboxylic acid ester formed in accordance with reaction equation (3), the acid portion has 1 more carbon atom than the starting olefin. Accordingly, various olefins can be selected according to the desired product. For example, in order to prepare acrylic acid esters, succinic acid esters or β-alkoxypropionic acid esters, ethylene is used as a starting olefin. In order to prepare higher carboxylic acids, the corresponding higher olefins can be used.

In the process of this invention, the reaction is carried out so that a diester of a carboxylic acid is obtained as a main product.

The olefins used in this invention are those containing 2 to 20 carbon atoms, and include, for example ethylene, propylene, 1-butene, 2-butene, isobutene, 1-pentene, 2-pentene, cyclopentene, 2-methylbutene-1, 2-methylbutene-2, 1-hexene, 2-hexene, 3-hexene, cyclohexene, 2-ethylbutene-1, 2-methylpentene-1, heptene-1, heptene-2, heptene-3, 2-ethylhexene-3, cycloheptene, isooctene, cyclooctene, 1-ethylcyclohexene, 1-nonene, isononene, 1-decene, 1-butylcyclohexene, 1,3-diethylcyclohexene, isodecene, indene, styrene, and α-methylstyrene.

Of these olefins, those having at least one of which oxidizable hydrogen atoms bonded to a carbon to form an unsaturated bond, especially ethylene, are preferred.

The monohydric aliphatic alcohols used in this invention are those containing 1 to 20 carbon atoms. Examples are methanol, ethanol, n-propanol, iso-propanol, n-butanol, sec-butanol, iso-butanol, n-pentanol, iso-pentanol, sec-pentanol, hexanol, heptanol, octanol, and decanol.

The aliphatic alcohol may be used in excess to cause it to function concurrently as a reaction solvent. If desired, other reaction solvents which are liquid under the reaction conditions and inert to the reaction mixture and the reaction product can be used. Examples of these solvents are ethers such as methyl ethyl ether, dimethyl ether, diisopropyl ether, anisole, ethylene glycol methyl ether, ethyl phenyl ether, diethylene glycol diethyl ether, triethylene glycol dimethyl ether and tetrahydrofuran; esters such as methyl formate, ethyl formate, n-propyl formate, iso-propyl formate, n-butyl formate, iso-propyl formate, n-butyl formate, sec-butyl formate, sec-butyl formate, phenyl formate, methyl acetate, ethyl acetate, n-propyl acetate, iso-propyl acetate, n-butyl acetate, sec-butyl acetate, iso-butyl acetate, phenyl acetate, n-amyl acetate, $HCOOCH_2CH_2COOCH$, $CH_3CO_2CH_2CH_2O_2CCH_3$, $CH_3COCH_2CO_2C_2H_5$, $CH_3COCH_2CO_2CH_3$, methyl benzoate, ethyl benzoate and ethylene carbonate; saturated aliphatic hydrocarbons such as pentane, hexane, heptane, octane, isooctane, cyclohexane, or cyclopentane; and aromatic hydrocarbons such as benzene, toluene, o-xylene, m-xylene or p-xylene.

The above reaction proceeds under very mild conditions. For example, the reaction is carried out at room temperature to a temperature of about 350° C., preferably about 50° C. to about 350° C. The total reaction pressure may be from atmospheric pressure to about 300 atmospheres. Preferably, the partial pressure of carbon monoxide during the reaction is at least about 1 atmosphere, and especially preferably, it is at least about 5 atmospheres.

The reaction system is preferably anhydrous, but needs not to be completely anhydrous. Even in the presence of some water, the reaction proceeds. For example, the above reaction proceeds even when the reaction system contains about 3% by weight of water.

The reaction in the present invention can be carried out either in the vapor phase or in the liquid phase, but preferably, it is performed in the liquid phase. Furthermore, any known method of catalytic reaction, such as a fixed bed method or a suspended catalyst bed method, can be used, and the reaction can be performed either batchwise or continuously. According to one example of the process of this invention, the catalyst composition is suspended in a reaction medium comprising an alcohol, and an olefin is fed into the suspension. Carbon monoxide under pressure is then introduced into the reaction mixture, and a gas containing molecular oxygen is blown into it at a predetermined temperature. The gas containing molecular oxygen needs not always be pure oxygen, but may be air or a mixture of oxygen and another gas not detrimental to the reaction, for example, an inert gas such as nitrogen. The amount of oxygen is not critical, but the concentration of oxygen is preferably such that it may not induce explosion in the reaction system. The preferred partial oxygen pressure is 0.1 to 20 atmospheres, preferably 0.2 to 10 atmospheres, and should not exceed 50% of the total pressure.

If desired, a suitable dehydrating agent can be used in order to maintain the reaction system anhydrous. Examples of organic dehydrating agents are alkyl- or aryl-isocyanates such as methyl isocyanate, benzene isocyanate, toluylene diisocyanate, and amyl isocyanate, N,N'-alkyl or N,N'-aryl substituted carbodiimides such as N,N'-dimethyl carbodiimide, N,N'-diethyl carbodiimide, and N,N'-diphenyl carbodiimide, various alkyl acetals such as 1,1-diethoxyethane, 1,1-dibutoxyethane, 2,2-dimethoxypropane and 2,2-diethoxypropane, and alkyl ortho-esters such as ethyl ortho-formate or methyl ortho-acetate.

The molar ratio of olefin to carbon monoxide in the reaction system can be varied over a wide range, but preferably, it is 1:50 to 50:1, more preferably 1:10 to 10:1.

According to the process of this invention, the olefin, monohydric aliphatic alcohol and carbon monoxide are subjected to oxidative carbonylation in an atmosphere containing molecular oxygen at room temperature to about 350° C. using a catalyst comprising, supported on a carrier, a post-reduced compound of a platinum group metal and a post-reduced compound of a metal having an atomic number of not less than 22 selected from the group consisting of metals of Groups Ib, IIb, III, IV, V, VI and VIIb, thereby to form diesters of carboxylic acids.

The term "post-reduced", as used in the present application, means that the above catalyst ingredients are supported on a carrier, and then subjected to a reducing treatment.

The platinum group metals that can be used in this invention are Ru, Rh, Pd, Os, Ir, Pt and mixtures of at least two of these metals. The use of Pd is especially preferred from the viewpoint of cost and activity. The compounds of the platinum group metal are preferably those soluble in aqueous or other liquid media. Examples of preferred compounds containing platinum group metals are soluble halides, soluble organic acid salts, soluble inorganic acid salts, and soluble oxides of the platinum group metals. For example, in the case of palladium, specific examples of palladium compounds that can be used in the present invention are palladium halides such as palladium chloride, or sodium palladium chloride, inorganic acid salts of palladium such as palladium nitrate and palladium sulfate, and oxides of palladium such as palladium oxide. Examples of other compounds containing platinum group metals include rhodium nitrate, rhodium chloride, chloroplatinic acid, platinum nitrate, iridium chloride, ruthenium chloride, and osmium oxide.

Complexes and chelates of the platinum group metals can also be used.

Examples of preferred metals having an atomic number of not less than 22 are metals of Group Ib selected from Cu and Au; metals of Group III selected from Y, In, lanthanoid metals, Th and U; metals of Group IV selected from Ti, Ge, Zr and Hf; metals of Group V selected from V, Sb and Bi; metals of Group VI selected from Mo and W; and metals of Group VII selected from Mn and Re. Of these, the metals of Groups III and IV are especially preferred. Specific examples of the lanthanoid metals in Group III are La, Nd, Sm, Eu, Tb, Dy, Ce and Ho.

Preferred compounds of these metals are those soluble in aqueous or other liquid media. Examples include soluble salts, halides, oxides, hydroxides, complexes, chelates and oxo acid compounds of these metals.

Examples of the salts, halides, complexes and chelates described above are organic acid salts such as formates, oxalates and acetates, inorganic acid salts such as nitrates and sulfates, halides such as chlorides, bromides and iodides, chelates such as acetylacetone, tartaric acid, ethylenediaminetetraacetic acid, or malonic acid; and oxo acid compounds such as chromic acid, vanadic acid, molybdic acid, tungstic acid, and salts thereof.

The carrier used to form carrier-supported catalysts used in this invention may be any inert solid carrier which assumes a solid state under the reaction conditions. Examples of preferred carriers include not only carbonaceous solid carriers such as activated carbon or graphite, but also silica, alumina, silica-alumina, zirconia, mordenite, molecular sieves such as X-type and Y-type zeolites, diatomaceous earth, magnesia, bauxite, and pumice. Examples of the graphite used as a carrier are naturally occurring graphite, graphite obtained by treatment of coal pitch, coke or petroleum pitch coke at high temperatures, graphite obtained by treatment of such gases as methane or ethane at high temperatures, or graphite obtained by high temperature treatment of activated carbon. Such graphite may of course be those having a graphatization degree of 100%, but also those semi-graphatized carbonaceous meterials having a graphatization degree of 10% or more.

In the process of this invention, the use of carbonaceous solid carriers is preferred.

Prior to use, the catalyst supported on a carrier used in this invention is subjected to a reducing treatment to reduce the platinum group metal-containing compound and the metal-containing compound on the carrier.

In order to support the catalyst compounds on the carrier, the platinum group metal-containing compound and the metal-containing compound are dissolved in a suitable solvent, and the solvent is impregnated in the carrier, followed by evaporating the solvent. The deposition of the catalyst compounds on the carrier can also be performed by adding an alkaline substance such as ammonia, urea, sodium hydroxide or pyridine as a precipitant to a mixture of the carrier and the above solution containing the platinum group metal-containing compound and the metal compound to deposit the catalyst compounds on the carrier, and then evaporating the solvent. In the above deposition procedure, the platinum group metal-containing compound and the metal compound may be deposited at the same time, or one of them is first deposited and then the other.

Examples of the solvent used to dissolve the catalyst compounds are water, methanol, ethanol, propanol, acetone, methyl ethyl ketone, acetic acid, propionic acid, ether, tetrahydrofuran, dioxane, methyl acetate, ethyl acetate, and mixtures thereof.

After depositing the catalyst compounds on the carrier, the resulting catalyst is subjected to a reducing treatment. As will be shown later in comparative examples, if this reducing treatment is omitted, the object of improvement in accordance with this invention is difficult to achieve. Reduction can be performed by heating in the presence of a reducing agent. Examples of the reducing agent are hydrogen, lower hydrocarbons such as methane, ethane or propane, and lower alcohols such as methanol or ethanol (reducing agents of group A). When using the reducing agents of group A, the reduction is preferably carried out in the vapor phase using an inert gas such as nitrogen, helium, neon, argon or carbon dioxide. The preferred reducing temperature is 150° to 550° C., more preferably 200° to 500° C. Other examples of the reducing agent are hydrazine and formaldehyde (reducing agents of group B). The preferred reaction temperature is −10° C. to 100° C., more preferably 0° to 100° C.

Preferably, the reduction is carried out so that at least a part of the compound of the metal of the above groups of the periodic table is reduced to a metal. The reducing time that brings about optimum activities of the catalyst can be easily determined experimentally according to the reducing temperature and the type of the metal compounds used. A precise chemical form of the catalyst compounds after reduction is not known, but it will be readily understood by comparing the results of the Examples with those of the Comparative Examples disclosed herein that the reduction treatment results in a marked improvement of the catalytic activity over those not subjected to the reducing treatment.

There is no particular restriction on the amount of the platinum group metal-containing compound to be supported on the carrier. Usually, the amount of the platinum group metal-containing compound is preferably about 0.01 to about 30% by weight, more preferably up to about 25% by weight, especially preferably up to about 20% by weight, calculated as the platinum group metal based on the weight of the carrier. The amount is the same for the compounds of the metals having an atomic number of not less than 22.

The ratio of the metal compound having an atomic number of not less than 22 to the platinum group metal-containing compound can also be changed suitably, and usually, the proportion of the metal compound is preferably 0.0005 to 10 gram atoms, more preferably about 0.005 to about 5 gram atoms, per gram atom of the platinum group metal-containing compound or compounds.

The carrier-supported catalysts used in this invention may contain as a promotor at least one of the salts, chelates, hydroxides, and oxides of alkali metals and alkaline earth metals. Specific examples of the promotor are potassium acetate, sodium hydroxide, lithium chloride, calcium carbonate, barium oxide, strontium formate, and magnesium chloride.

The amount of the promotor can be suitably selected. For example, the preferred amount is 0.01 to 5% by weight based on the weight of the carrier, calculated as the alkali metal and/or alkaline earth metal.

The amount of the carrier-supported catalyst can be properly selected in performing the process of this invention. Preferably, the amount of the catalyst is about 0.001 to about 5% by weight calculated as the amount of the platinum group metal based on the reaction medium.

According to the process of this invention described in detail above, esters, especially diesters of dicarboxylic acids, can be obtained from olefins in high yields and selectivities. In addition, the loss of the precious catalyst ingredient can be substantially prevented, and post-treatments for recovering the final product are easy. These advantages render the process very suitable for commercial operation.

The following Examples and Comparative Examples illustrate the process of this invention in greater detail.

EXAMPLES OF CATALYST PREPARATION 1.79 g of palladium chloride (1.08 g as Pd metal) was dissolved in 100 ml of 6N hydrochloric acid, and 10.0 g of activated carbon with a size of 100–150 mesh as a carrier was added. The mixture was thoroughly stirred, and evaporated to dryness at 50° to 100° C. The dried product was added to 0.1 liter of a solution containing each of the metal compounds shown in Table 1, and the mixture was evaporated to dryness at 50° to 100° C. The resulting catalyst compounds on the carrier was dried in an atmosphere of nitrogen at 150° C. for 10 hours. A gaseous mixture consisting of $H_2$ and $N_2$ in a volume ratio of 1 to 4 was passed through the resulting catalyst at a rate of 1 liter/min. at 400° C. for 10 hours thereby to form a catalyst.

Table 1

| Catalyst No. | Metal compound | Solvent (the figures are volume ratios) | Amount supported (as metal) | |
|---|---|---|---|---|
| | | | Pd (wt.% based on the carrier weight) | Metal (wt. % based on the carrier weight) |
| 1 | $YCl_3$ | Acetone/water/alcohol (=40/$\frac{1}{2}$) | 10 | 2 |
| 2 | $In(NO_3)_3$ | Water/acetone (=1/40) | 10 | 2 |
| 3 | $La(NO_3)_3$ | Acetone | 10 | 0.5 |
| 4 | $NdCl_3$ | Acetone | 10 | 0.5 |
| 5 | $SmCl_3$ | Acetone | 10 | 0.5 |
| 6 | $EuCl_3$ | Water/acetone (=2/40) | 10 | 0.5 |
| 7 | $DyCl_3$ | Acetone/water/alcohol (=40/$\frac{1}{2}$) | 10 | 0.5 |
| 8 | $TbCl_3$ | " | 10 | 0.5 |
| 9 | $HoCl_4$ | " | 10 | 0.5 |
| 10 | $TiCl_4$ | Acetone | 10 | 1.0 |
| 11 | $GeO_2$ | Water | 10 | 1.0 |
| 12 | $ZrCl_4$ | Ethanol/acetone (=2/40) | 10 | 1.0 |
| 13 | $HfCl_4$ | Acetone | 10 | 1.0 |
| 14 | $CeCl_3$ | Ethanol/acetone (=2/20) | 10 | 0.5 |
| 15 | $CuCl_2$ | Ethanol/acetone (=2/20) | 10 | 2 |
| 16 | $AuCl_4$ | Acetone | 10 | 2 |
| 17 | $VCl_4$ | Acetone | 1.0 | 2 |
| 18 | $SbCl_4$ | Acetone | 1.0 | 2 |
| 19 | $BiCl_3$ | 6N HCl | 1.0 | 2 |
| 20 | $MoCl_3$ | 6N HCl | 2 | 2 |
| 21 | $WCl_4$ | Ethanol | 10 | 1 |
| 22 | $MnCl_2$ | Water | 10 | 1 |
| 23 | $ReO_7$ | Water | 10 | 1 |
| 24 | $Th(NO_3)_3$ | Water | 10 | 1 |
| 25 | $UO_2(CH_3COO)_2$ | Acetone/water (=40/20) | 10 | 1 |

EXAMPLES 1 TO 25 AND COMPARATIVE EXAMPLES 1 TO 25

A 300 ml. autoclave equipped with an electromagnetically stirring means and a thermometer was charged with 3.0 g of each of the catalysts obtained in the above Example of Catalyst Preparation and 150 ml. of dehydrated methanol. Ethylene and carbon monoxide were introduced a gauge pressure of 55 atmospheres and 36 atmospheres, respectively, and then the temperature inside the autoclave was elevated to the points shown in Table 2. Oxygen gas was then introduced portionwise at increments of 2 atmospheres to a total pressure of 14 atmospheres, and the reaction was performed for 5 hours. The results are shown in Table 2.

Table 2 also contains the results obtained by using non-reduced catalysts which had been prepared in the same way as in the Example of Catalyst Preparation except that reducing treatment was not effected. Such catalysts are shown in Table 2 by attaching primes to the corresponding catalyst numbers.

The results of Table 2 demonstrate that the process of this invention give diesters of carboxylic acids in very good yields and selectivities.

EXAMPLES 26 and 27 AND COMPARATIVE EXAMPLES 26 AND 27

Using 5.0 g of each of the same catalysts as used in Examples 12, 12' (comparison), and Examples 13 and 13' (comparison) shown in Table 1, the reaction was carried out continuously for a long period of time at 140° C. and 70 atms. (gauge) in a 200 ml. autoclave equipped with an electromagnetically stirring means, a thermometer and a decanter. The vapor in the autoclave was continuously withdrawn at a rate of 200 ml./min. from the vapor phase of the autoclave. On the other hand, a gaseous mixture of ethylene, carbon monoxide and oxygen in a volume ratio of 50:30:3 was continuously fed into the liquid phase inside the autoclave so that the pressure inside the autoclave was maintained at 70 atms. (gauge). Dehydrated methanol was fed into the autoclave at a rate of 50 ml./hour while a part of the product was being withdrawn from the autoclave so that the volume of the liquid phase in the autoclave was maintained at 150 ml. during the reaction. The products Table 2

| Runs (Example = Ex.; Comparative Example = Comp.) | Catalyst No. | Reaction temperature (° C) | Main product Dimethyl succinate (gr) | By-Products Methyl acrylate (gr) | Methoxy-propionic acid (gr) | Other products such as methyl propionate dimethyl oxalate and dimethyl carbonate (gr) | Yield of the main product (%) | Selectivity to the main product** (mol %) |
|---|---|---|---|---|---|---|---|---|
| Ex. 1 | No. 1 | 140 | 10.6 | 0.39 | 0.11 | 0.12 | 19.9 | 92.6 |
| Comp. 1 | No. 1' | 140 | 8.1 | 0.74 | 0.23 | 0.13 | 15.0 | 83.4 |
| Ex. 2 | No. 2 | 140 | 11.3 | 0.34 | 0.07 | 0.22 | 21.0 | 93.7 |
| Comp. 2 | No. 2' | 140 | 8.6 | 0.73 | 0.11 | 0.51 | 16.0 | 85.9 |
| Ex. 3 | No. 3 | 130 | 12.6 | 0.21 | 0.16 | 0.25 | 23.4 | 95.7 |
| Comp. 3 | No. 3' | 130 | 7.9 | 0.72 | 0.25 | 0.21 | 14.7 | 83.6 |
| Ex. 4 | No. 4 | 130 | 11.5 | 0.37 | 0.09 | 0.21 | 21.4 | 93.8 |
| Comp. 4 | No. 4' | 130 | 8.0 | 0.66 | 0.14 | 0.28 | 14.9 | 85.6 |
| Ex. 5 | No. 5 | 130 | 11.7 | 0.29 | 0.03 | 0.14 | 21.8 | 95.4 |
| Comp. 5 | No. 5' | 130 | 8.8 | 0.71 | 0.12 | 0.23 | 16.4 | 86.5 |
| Ex. 6 | No. 6 | 130 | 11.6 | 0.28 | 0.02 | 0.17 | 21.6 | 95.7 |
| Comp. 6 | No. 6' | 130 | 8.7 | 0.46 | 0.31 | 0.26 | 16.2 | 88.1 |
| Ex. 7 | No. 7 | 130 | 12.1 | 0.35 | 0.03 | 0.04 | 22.5 | 94.9 |
| Comp. 7 | No. 7' | 130 | 7.9 | 0.63 | 0.10 | 0.25 | 14.7 | 86.7 |
| Ex. 8 | No. 8 | 130 | 12.2 | 0.42 | 0.07 | 0.15 | 22.7 | 93.7 |
| Comp. 8 | No. 8' | 130 | 8.3 | 0.62 | 0.16 | 0.32 | 15.4 | 86.6 |
| Ex. 9 | No. 9 | " | 12.4 | 0.26 | 0.13 | 0.18 | 23.1 | 95.3 |
| Comp. 9 | No. 9' | " | 8.4 | 0.52 | 0.26 | 0.44 | 15.6 | 87.2 |
| Ex. 10 | No. 10 | 135 | 12.9 | 0.07 | 0.09 | 0.06 | 24.0 | 98.1 |
| Comp. 10 | No. 10' | " | 8.5 | 0.64 | 0.14 | 0.35 | 15.8 | 86.9 |
| Ex. 11 | No. 11 | " | 12.8 | 0.14 | 0.09 | 0.09 | 23.8 | 97.2 |
| Comp. 11 | No. 11' | 135 | 8.8 | 0.77 | 0.09 | 0.51 | 16.4 | 86.0 |
| Ex. 12 | No. 12 | " | 13.1 | 0.14 | trace | 0.02 | 24.4 | 98.1 |
| Comp. 12 | No. 12' | " | 8.3 | 0.43 | 0.21 | 0.81 | 15.4 | 88.9 |
| Ex. 13 | No. 13 | " | 13.3 | 0.11 | trace | 0.07 | 24.7 | 98.5 |
| Comp. 13 | No. 13' | " | 8.4 | 0.45 | 0.16 | 0.96 | 15.6 | 89.1 |
| Ex. 14 | No. 14 | 130 | 12.2 | 0.16 | 0.04 | 0.23 | 22.7 | 97.2 |
| Comp. 14 | No. 14' | " | 8.2 | 0.64 | 0.14 | 0.42 | 15.3 | 86.2 |
| Ex. 15 | No. 15 | 140 | 9.7 | 0.46 | 0.13 | 0.48 | 18.0 | 90.9 |
| Comp. 15 | No. 15' | " | 8.9 | 0.53 | 0.20 | 1.20 | 16.6 | 86.9 |
| Ex. 16 | No. 16 | " | 10.5 | 0.36 | 0.18 | 0.26 | 19.5 | 92.5 |
| Comp. 16 | No. 16' | " | 8.2 | 0.64 | 0.21 | 0.73 | 15.2 | 85.5 |
| Ex. 17 | No. 17 | " | 9.4 | 0.42 | 0.11 | 0.09 | 17.5 | 91.7 |
| Comp. 17 | No. 17' | " | 7.8 | 0.64 | 0.09 | 0.88 | 14.5 | 85.0 |
| Ex. 18 | No. 18 | 140 | 9.3 | 0.36 | 0.22 | 0.27 | 17.3 | 91.2 |
| Comp. 18 | No. 18' | " | 8.6 | 0.52 | 0.12 | 0.73 | 16.0 | 88.7 |
| Ex. 19 | No. 19 | " | 9.7 | 0.41 | 0.18 | 0.37 | 18.0 | 91.1 |
| Comp. 19 | No. 19' | " | 8.2 | 0.56 | 0.10 | 0.87 | 15.3 | 87.5 |
| Ex. 20 | No. 20 | " | 10.1 | 0.32 | 0.09 | 0.46 | 18.8 | 93.5 |
| Comp. 20 | No. 20' | " | 7.7 | 0.95 | 0.11 | 0.13 | 14.3 | 81.4 |
| Ex. 21 | No. 21 | " | 9.9 | 0.34 | 0.25 | 0.26 | 18.4 | 91.6 |
| Comp. 21 | No. 21' | " | 7.3 | 0.47 | 0.10 | 0.91 | 13.6 | 88.3 |
| Ex. 22 | No. 22 | " | 10.2 | 0.52 | 0.03 | 0.47 | 19.0 | 91.5 |
| Comp. 22 | No. 22' | " | 7.8 | 0.46 | 0.11 | 0.96 | 14.5 | 88.1 |
| Ex. 23 | No. 23 | " | 9.2 | 0.35 | 0.20 | 0.13 | 17.1 | 91.5 |
| Comp. 23 | No. 23' | " | 8.6 | 2.51 | 1.19 | 0.70 | 16.0 | 59.8 |
| Ex. 24 | No. 24 | 140 | 12.5 | 0.33 | 0.15 | 0.14 | 23.3 | 94.3 |
| Comp. 24 | No. 24' | " | 8.5 | 0.74 | 0.45 | 0.42 | 15.8 | 82.0 |
| Ex. 25 | No. 25 | " | 12.3 | 0.22 | 0.11 | 0.10 | 22.9 | 95.8 |
| Comp. 25 | No. 25' | " | 8.8 | 0.89 | 0.11 | 0.54 | 16.4 | 83.7 |

*The yield is the amount (mol %) of the main product based on ethylene charged.
**The selectivity (mol %) is the percentage of the mols of dimethyl succinate as a main product based on the total mols of the main product and the by-products.

obtained after a continuous reaction for 10 to 15 hours and 50 to 55 hours were analyzed for the amount of dimethyl succinate as a main product and its selectivity. The results are shown in Table 3.

Table 3

| Run | Catalyst No. | Reaction time (hours) | Amount of dimethyl succinate (gr) | Amount of dimethyl succinate per unit of catalyst (gr/hr. catalyst) | Selectivity to dimethyl succinate (%) |
|---|---|---|---|---|---|
| Ex. 26 | 12 | 10-15 | 15.1 | 0.60 | 98.0 |
|  |  | 50-55 | 14.7 | 0.59 | 98.0 |
| Comparative Ex. 26 | 12' | 10-15 | 2.5 | 0.10 | 91.0 |
|  |  | 50-55 | 0 | 0 | 0 |
| Ex. 27 | 13 | 10-15 | 15.5 | 0.62 | 97.7 |
|  |  | 50-55 | 14.1 | 0.56 | 98.1 |
| Comparative Ex. 27 | 13' | 10-15 | 5.3 | 0.21 | 90.5 |
|  |  | 50-55 | 0.3 | 0.01 | 92.1 |

EXAMPLES 28 to 31 AND COMPARATIVE EXAMPLES 28 TO 31

Example 1 was repeated except that the same catalysts as used in Examples 10, 10' (comparison). Examples 11, 11' (comparison), and Examples 3, 3' (comparison) were used, with the aliphatic alcohol and olefin changed as shown in Table 4. Carbon monoxide was introduced to a pressure of 50 atms. (gauge), and the reaction was carried out at 150° C. The alcohol was used in the same amount as the methanol used in Example 1. In the case of the olefin, 2-butene was used in an amount of 20.2 g, and cyclohexene, in an amount of 37.0 g. The results obtained are shown in Table 4.

Table 4

| Run | Catalyst No. | Raw materials Olefin | Alcohol | Amount of the diester formed (gr) |
|---|---|---|---|---|
| Ex. 28 | 10 | Ethylene | Propanol | 14.1 |
| Comp. Ex. 28 | 10' | Ethylene | Propanol | 9.8 |
| Ex. 29 | 11 | Ethylene | Butanol | 18.6 |
| Comp. Ex. 29 | 11' | Ethylene | Butanol | 11.4 |
| Ex. 30 | 3 | 2-Butene | Methanol | 13.9 |
| Comp. Ex. 30 | 3' | 2-Butene | Methanol | 10.1 |
| Ex. 31 | 3 | Cyclohexene | Methanol | 17.0 |
| Comp. Ex. 31 | 3' | Cyclohexene | Methanol | 10.3 |

What we claim is:

1. In a process for preparing diesters of carboxylic acids by oxidative carbonylation of $C_2$-$C_{20}$ olefins, $C_1$-$C_{20}$ alkanols, and carbon monoxide in an atmosphere containing molecular oxygen, at a temperature of from room temperature to about 350° C and at a pressure of from atmospheric to about 300 atmospheres, in the presence of a carrier-supported catalyst, the catalyst consisting essentially of (1) a compound of platinum group metal and (2) a compound of a metal having an atomic number of not less than 22 which is a metal of Groups Ib, IIb, III, IV, V, VI, or VIIb of the Periodic Table, the improvement comprising using said catalyst wherein the catalyst is reduced so that at least a part of compound (2) is reduced to a metal and the ratio of compound (2) to compound (1) is from 0.0005:1 to 10:1 gram-atoms.

2. The process of claim 1 wherein the metal of compound (2) is selected from the group consisting of Cu, Au, Y, In, La, Nd, Sm, Eu, Tb, Dy, Ce, Ho, Th, U, Ti, Ge, Zr, Hf, V, Sb, Bi, Mn, Re, Mo and W.

3. The process of claim 1 wherein the carrier is a solid carbonaceous material.

4. The process of claim 1 wherein the ratio of compound (2) to compound (1) is from 0.0005:1 to 5:1 gram-atoms.

5. The process of claim 1 wherein the catalyst is reduced by heating in the presence of a reducing agent selected from the group consisting of hydrogen, methane, ethane, propane, methanol and ethanol, and an inert gas at a temperature of from 150° C to 550° C.

6. The process of claim 5 wherein the reducing temperature is from 200° C to 500° C.

7. The process of claim 1 wherein the catalyst is reduced by contacting with hydrazine and formaldehyde at a temperature of −10° to 100° C.

8. The process of claim 7 wherein the reducing temperature is from 0° to 100° C.

9. The process of claim 1 wherein the metal of compound (1) is palladium, the metal of compound (2) is selected from the group consisting of Y, In, La, Nd, Sm, Eu, Dy, Tb, Ho, Ti, Ge, Zr, Hf, Ce, Cu, Au, V, Sb, Bi, Mo, W, Mn, Re, Th and U, and the carrier is activated carbon having a size of 100-150 mesh, the catalyst being reduced by passing a gaseous mixture consisting essentially of $N_2$ and $H_2$ in a volume ratio of 1 to 4 at a rate of 1 liter/min. at 400° C for 10 hours.

* * * * *